United States Patent [19]

Muchowski et al.

[11] Patent Number: 4,543,361
[45] Date of Patent: Sep. 24, 1985

[54] ±2-[PHENETHYL]-5-[(3,4-METHYLENEDI-OXY)-α-HYDROXYBENZYL]PYRROLIDINE ANTIHYPERTENSIVES AND USE THEREAS

[76] Inventors: Joseph M. Muchowski; Robert Greenhouse; Jack Ackrell; Tsung-Tee Li; Jurg R. Pfister, all of 3401 Hillview Ave., P.O. Box 10850, Palo Alto, Calif. 94303

[21] Appl. No.: 527,717

[22] Filed: Aug. 29, 1983

[51] Int. Cl.$^4$ .................... A61K 31/40; C07D 405/02
[52] U.S. Cl. ........................................ 514/422; 548/526
[58] Field of Search ..................... 548/526; 424/274

[56] References Cited

U.S. PATENT DOCUMENTS 4,372,692  8/1982  Suh et al. ........................... 548/526

Primary Examiner—Glennon H. Hollrah
Assistant Examiner—D. B. Springer
Attorney, Agent, or Firm—Ellen J. Buckles; Tom M. Moran; Alan M. Krubiner

[57] ABSTRACT

A compound of the formula

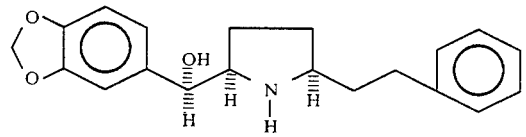

and the pharmaceutically acceptable acid addition salts thereof are potent antihypertensive agents and are therefore useful as cardiovascular system regulators.

9 Claims, No Drawings

±2-[PHENETHYL]-5-[(3,4-METHYLENEDIOXY)-α-HYDROXYBENZYL]PYRROLIDINE ANTIHYPERTENSIVES AND USE THEREAS

BACKGROUND OF THE INVENTION

1. Field of the Invention

This invention concerns ±2-[phenethyl]-5-[(3,4-methylenedioxy)-α-hydroxybenzyl]pyrrolidines which affect the cardiovascular system and which are particularly effective as antihypertensive agents. The invention is directed toward orally active, long lasting cardiovascular regulators of hypertension.

The invention also concerns a method for regulating the cardiovascular system and managing the hypertension, and a pharmaceutical composition comprising of the compound of this invention as an active ingredient.

2. Related Disclosures

The invention herein concerns cyclic analogs of compounds known to possess molecular segments which affect peripheral nervous system receptors regulating the cardiovascular system. These compounds are also effective as bronchodilators.

Various physiological responses result from administering pharmaceuticals which affect the cardiovascular system regulating receptors. These responses may vary from vasodilation, vasoconstriction, tachycardia, bradycardia, positive or negative inotropic effect. Secondary effects such as bronchodilation or bronchoconstriction can also appear.

The physiological response depends on the exact nature of the drug. Therefore, various members of the same general class of compounds may be used in the treatment of cardiac disorders such as hypertension, cardiac arrhythmia, and vasal congestion.

The following resume represents a compilation of the known compounds which most closely resemble, in molecular structure, the compounds of the present invention, and which are useful in treating cardiovascular disorders and in other therapeutic applications.

Practolol and prenalterol which are amino-alcohol aryl ethers are well known and commercially available compounds which affect the α₁ adrenergic receptors of the peripheral system.

Sulfinolol, (British Pat. No. 1,544,872, published Apr. 25, 1979) and its relatives, are known antihypertensive/antiarrhythmic agents.

Deliberate attempts to combine $\alpha_1$ affectors with vasodilators resulted in compounds such as naphthalenone phthalazinylhydrazones. Naphthalenone phthalazinylhydrazones may be hydrolyzed in the body to form a well known peripheral vasodilator hydralazine, and a general $\alpha$ adrenergic blocker bunolol, (see U.S. Pat. No. 4,061,636).

Cyclic compounds containing a 5 or 6 membered saturated nitrogen-containing ring, linked through a hydroxymethyl group to an aromatic nucleus, such as, for example, rimeterol (Pinder, R. M. et al, *Drugs*, 14:81 (1977)) and other compounds disclosed in European Pat. No. 10460, published Apr. 30, 1980 are known psychotropic and hypolipaemic agents. Rimeterol, itself, is a known $\alpha_2$ agonist which is effective when given parentherally, but not effective when administered orally. Some of these compounds have recently been described as having hypotensive effect (See European Pat. No. 22408).

British Pat. No. 1,392,674, published Apr. 30, 1975, discloses compounds related in structure to those of the current invention which are useful for treatment of acute slowdown cardiac contractility.

U.S. Pat. No. 4,342,692 and its EPO counterpart disclose a family of compounds which may be interpreted to be similar to the compounds of the current invention. U.S. Pat. No. 3,655,693 discloses salicylic acid derivatives useful in the treatment of inflammation. U.S. Pat. No. 3,984,200 discloses mono or dihydroxyphenylalkyl dopamine derivatives useful as inotropic agents.

The present invention is directed toward orally active, long lasting cardiovascular regulators. The compounds combine, in a sterically controlled way, two segments related to structures showing analogous activities (i.e. an arylhydroxymethyl or benzyl moiety bridged through a short chain to nitrogen and another aromatic group also linked to a nitrogen), by joining these through a common nitrogen atom cyclized to form a pyrrolidine ring.

The compound of this invention have a strong antihypertensive activity. The antihypertensive activity of the compounds of this invention is best shown by their effect on the systolic blood pressure. The compounds of this invention decrease significantly the systolic blood presure without at the same time increasing heart rates. Moreover, the dosage which is needed to decrease systolic blood pressure is very low and the secondary, often undesirable, side effects are thus avoided. Thus, this invention offers the effective management of hypertension without submitting the treated subject to the undesirable secondary effects which would be unavoidable if large doses are needed.

SUMMARY OF THE INVENTION

The invention herein relates to compounds of the formula

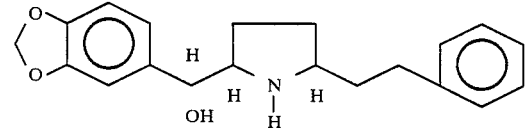

and their pharmaceutically acceptable acid addition salts. These compounds are potent antihypertensive agents and are therefore useful as cardiovascular system regulators.

The other aspect of this invention relates to the mixture of and to individual stereoisomers, namely cis erythro, cis threo, trans erythro and trans threo isomers of the above compounds.

DETAILED DESCRIPTION OF THE INVENTION

Definitions

As used hereinafter:

"Noble metal catalyst" is a catalyst such as platinum on carbon, platinum oxide, palladium on carbon, or rhodium on carbon, but other noble metal catalysts suitable to effect catalytic reductions are also included.

"Protection" or "Protecting group" refer to the protection of phenolic hydroxyl groups. A phenolic hydroxyl group is present in many compounds prepared by the process of this invention. In order to preserve the phenolic hydroxyl group during the catalytic reduction, O-protection is often required for phenols, which react readily with oxidizing agents, electrophiles, or even with mild alkylating and acylating agents. The protection of phenolic hydroxyl groups can be achieved with any suitable protecting group such as an alkyl ether, for example methyl ether, isopropyl ether, t-butyl ether; alkoxymethyl ether, for example methoxymethyl ether; alkoxyethoxymethyl ether, for example methoxyethoxymethyl ether; cycloalkylmethyl ether, for example cyclopropylmethyl ether; alkyldimethylsilyl ether, for example t-butyldimethylsilyl ether, 9-anthrylmethyl ether, preferably substituted or unsubstituted benzyl ether. [*Protective Groups in Organic Synthesis*, John Wiley & Sons, New York, pp:87-100(1980); Synthesis, (II): 987 (1982)].

"N-Protection" or "N-Protecting groups" refer toelectron withdrawing groups which make pyrrole less aromatic and more susceptible to the reduction. Electron withdrawal achieved through the utilization of N-protection of the nitrogen atom of the pyrrole can be best illustrated by attachment of the acyl N-protecting group, i.e.

where R may be aryl, phenyl, substituted phenyl, alkyl of 1-4 carbons with branched alkyl preferred, alkoxy of 1-4 carbons with branched alkoxy preferred. Exemplary N-protecting groups for the pyrrole nitrogen atom are alkoxycarbonyl such as methoxycarbonyl, ethoxycarbonyl, propoxycarbonyl, t-butoxycarbonyl and the like, or alkylcarbonyl such as methylcarbonyl, ethylcarbonyl, propylcarbonyl and the like, or alkanoyl such as ethanoyl, propanoyl, butanoyl and the like, or aroyl. These groups are also called 1-$R_2$-protecting groups in this application.

"Aroyl" means the radical ZCO— wherein Z is an aromatic group such as, for example, benzoyl or naphthoyl.

"Wt %" (weight percent) used for solids means the weight of one solid relative to the total weight of all reactants. For example, if 10 wt % of catalyst is given, then 10 g of catalyst are added for 90 g of other reactants.

"Mild reaction conditions" means that the reaction is run at the low temperatures between 10°-35° C., preferably ambient, and at pressures of 1-5 atmospheres, preferably at atmospheric pressure, in the presence of a suitable polar organic solvent.

"Organic solvent" means liquid organic compound with the power to dissolve solids or liquids at mild reaction conditions. The term is meant to include cyclic and acyclic compounds such as alcohols of 1-4 carbons, lower alkyl esters of alkanoic acids, ethers, cyclic ethers and the like. Exemplary solvents are methanol, ethanol, ethyl acetate, tetrahydrofuran, benzene or mixtures thereof.

"Lower alkyl" means a branched or unbranched saturated hydrocarbon chain containing from one to four carbon atoms, such as, for example, methyl, ethyl, n-propyl, iso-propyl, n-butyl, iso-butyl and the like.

"Cycloalkyl" means a saturated monocyclic hydrocarbon of 3-7 carbons without side chains, such as cyclopropane, cyclobutane, cyclopentane, cyclohexane and cycloheptane.

"Alkoxy" means —OR wherein R is lower alkyl as defined hereinabove.

"Alkoxycarbonyl" means —C(O)—OR wherein R is lower alkyl as defined hereinabove.

"Alkylcarbonyl" means —C(O)—R wherein R is lower alkyl as defined hereinabove.

Hereinafter "α-hydroxybenzyl" or "phenylhydroxymethyl" means compounds of the formula

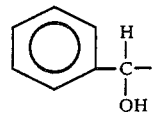

"Strong acid" means an organic or inorganic, water soluble, easily dissociable Bronsted Lowry acid, such as methanesulfonic, trifluoroacetic, hydrochloric, sulfuric, phosphoric acid and the like.

"Strong base" means an inorganic, water soluble base such as sodium hydroxide, sodium carbonate, potassium carbonate, and the like.

"N-acylating" means the formation or introduction of acyl radical

to the N-atom of the pyrrole ring.

STEREOCHEMICAL CONTROL

The ±2-[phenethyl]-5-[(3,4-methylenedioxy)-α-hydroxybenzyl]pyrrolidines have three chiral centers. Two chiral centers are at the 2- and 5-positions of the pyrrolidine ring at which the side chains are substituted. The third chiral center is introduced in pyrrolidines where the side chain attached to the 5-position is α-hydroxybenzyl.

Compounds with three chiral centers can be obtained as four diastereoisomeric racemates or as eight optical isomers in total. The nomenclature (±)cis erythro, (±)cis threo, (±)trans erythro and (±)trans threo is used to describe individual diastereoisomers.

Embodiments wherein hydrogens at 2- and 5-positions are on the same side of the plane of the pyrrolidine ring are designated "cis". Embodiments where hydrogens at 2- and 5-position are on opposite sides are "trans."

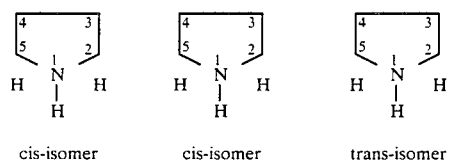

cis-isomer     cis-isomer     trans-isomer

"Erythro/threo" terminology is used to designate the relationship between the configurations of the group attached to the carbon atom bearing the hydroxyl substituent and of the number 5 carbon of the pyrrolidine ring to which it is attached.

"Erythro" indicates those embodiments wherein the hydrogen of carbon atom 5 of the ring and the hydrogen of the hydroxylated carbon occupy the same side of the molecule.

"Threo" indicates those embodiments where the hydrogen of carbon atom 5 of the ring and the hydrogen of the hydroxylated carbon are on the opposite sides of the molecule. For the numbering system, see below.

cis-erythro isomer    cis-threo isomer trans-erythro isomer    trans-threo isomer See *Stereochemistry of Carbon Compounds,* McGraw-Hill, pp. 16–86 (1962); *RECUEIL,* 83:535, (1964); and Morison and Boyd, *Organic Chemistry,* 3d Ed., pp. 148–153, (1974).

Numbering on the phenyl rings of the pyrrole or pyrrolidine molecule is illustrated below.

It is to be understood that this invention discloses and encompasses each of the racemates, racemic mixtures, diastereomers and enantiomers.

PREFERRED EMBODIMENTS

Presently preferred embodiments of this invention are compounds of the formula

±trans threo namely, ±trans threo 2-[phenethyl]-5-[(3,4-methylenedioxy)-α-hydroxybenzyl]pyrrolidine.

More preferred embodiments are compounds of the formula

±trans erythro namely, ±trans erythro 2-[phenethyl]-5-[(3,4-methylenedioxy)-α-hydroxybenzyl]pyrrolidine.

Other more preferred embodiments are compounds of the formula

±cis threo namely, ±cis threo 2-[phenethyl]-5-[(3,4-methylenedioxy)-α-hydroxybenzyl]pyrrolidine.

Most preferred embodiments are compounds of the formula

±cis erythro namely, ±cis erythro 2-[phenethyl]-5-[(3,4-methylenedioxy)-α-hydroxybenzyl]pyrrolidine.

PREPARATION PROCEDURES

A compounds of this invention are prepared by the reaction sequence illustrated in Reaction Schemes 1–4.

Reaction Scheme 1 illustrates the preparation of ±cis erythro 2-[phenethyl]-5-[3,4-methylenedioxy)-α-hydroxybenzyl]pyrrolidine. Reaction Scheme 2 illustrates the preparation of ±cis threo 2-[phenethyl]-5-[3,4-methylenedioxy)-α-hydroxybenzyl]pyrrolidine.

Reaction Scheme 3 illustrates preparation of ±trans erythro 2-[phenethyl]-5-[3,4-methylenedioxy)-α-hydroxybenzyl]pyrrolidine. Reaction Scheme 4 illustrates preparation of ±trans threo 2-[phenethyl]-5-[3,4-methylenedioxy)-α-hydroxybenzyl]pyrrolidine.

REACTION SCHEME 1

REACTION SCHEME 1
-continued

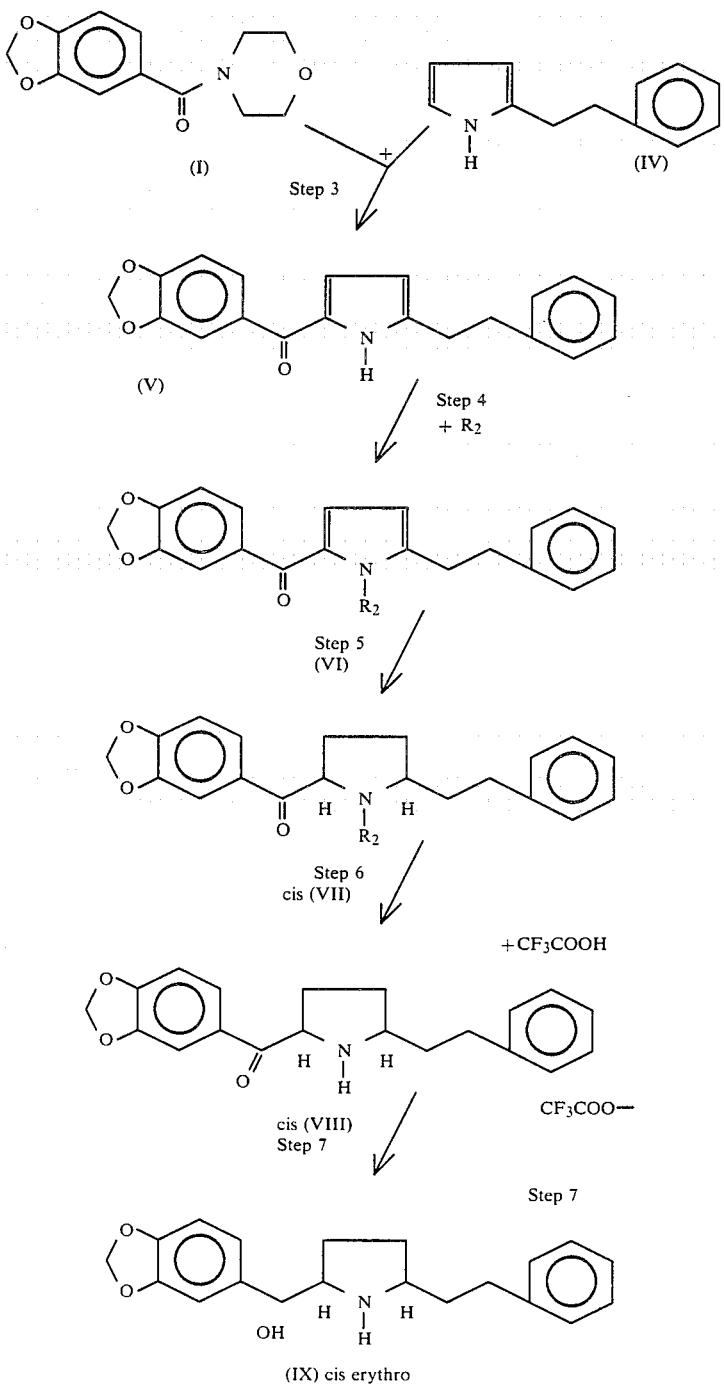

Step 1. Step 1 describes the preparation of phenylacetylpyrrole (III) from pyrrole (IIb) and phenylacetylmorpholide (IIa).

Pyrrole (IIb) is commercially available from Aldrich.

Phenylacetylmorpholide (IIa) is prepared by reacting phenylacetic acid with thionyl chloride and with a small amount of dimethylformamide for 10–60 minutes at room temperature. The resulting mixture is reacted with morpholine dissolved in an organic solvent, preferably in dry dichloromethane, to give phenylacetylmorpholide (II).

Phenylacetylmorpholide (IIa) in the presence of an acylating agent, such as acid halides, preferably in phosphorous oxychloride, is reacted under the constant stirring for 3–8 hours, preferably for 6 hours. Pyrrole (IIb) dissolved in a chlorinated hydrocarbon solvent, preferably in anhydrous 1,2-dichloroethane, is added. The reaction mixture is stirred for 12–20 hours, alkalized, and purified by methods known in the art to obtain phenylacetylpyrrole (III).

Step 2. Step 2 describes the conversion of phenylacetylpyrrole (III) to 2-[phenethyl]pyrrole (IV).

Compound (III) is dissolved in an ethereal solvent, preferably anhydrous tetrahydrofuran, and a complex metal hydride, preferably lithium aluminum hydride, is added. The mixture is reacted at reflux temperature for 35–53 hours, preferably 48 hours. Excess of hydride is destroyed with organic solvent and the reaction mixture is purified by methods known to the art to afford 2-[phenethyl]pyrrole (IV).

Step 3. Step 3 describes the preparation of 2-[phenethyl]-5-[(3,4-methylenedioxy)benzoyl]pyrrole (V).

[(3,4-Methylenedioxy)benzoyl]morpholide (I), is prepared from 3,4-methylenedioxybenzoic acid by procedure similar to that of Step 1. (For details, see Example 1.)

[(3,4-Methylenedioxy)benzoyl]morpholide is reacted with an acylating agent, preferably phosphorous oxychloride, at a room temperature for 1–5 hours. Then the compound (IV), dissolved in an organic solvent, preferably in 1,2-dichloroethane, is added and the mixture is stirred for 15–21 hours, preferably for 18 hours. The mixture is purified by methods known in the art to give ±2-[phenethyl]-5-[(3,4-methylenedioxy)benzoyl]pyrrole (V).

Step 4. Step 4 describes an attachment of the protective group $R_2$ to the N atom of the pyrrole compound (V).

Compound (V) is dissolved in a suspension of an ethereal or dipolar solvent, preferably in dry dimethylformamide, and mixed with sodium hydride. The mixture is heated to 45°–60° for 1–3 hours, preferably 2 hours. Suitable N-protecting agent $R_2$, such as aroylchloride, alkanoylchloride, alkylchloroformate, preferably di-t-butylcarbonate, is added and the mixture is stirred at 60°–70° for 1–3 hours. After purification and crystallization of methods known in the art, ±1-$R_2$-protected-2-[phenethyl]-5-[3,4-methylenedioxy)benzoyl]pyrrole, preferably 1-t-butoxycarbonyl-2-[phenethyl]-5-[(3,4-methylenedioxy)benzoyl]pyrrole (VI) is obtained.

Step 5. Step 5 describes a catalytic reduction of 1-t-butoxycarbonyl-2-[phenethyl]-5-[(3,4-methylenedioxy)benzoyl]pyrrolidine (VII).

Pyrrole (VI) is reduced in the presence of the noble metal catalyst, such as rhodium on carbon, rhodium on aluminum, platinum on carbon, preferably with platinic oxide, in the solvent or solvent mixture containing lower alcohol, lower alkyl ester or ethereal solvent. The solvent mixture preferred is ethanol-ethyl acetate. Reduction is carried on under the mild reaction conditions, at the room temperature and pressure of 1–3 atmospheres, preferably at atmospheric pressure for 15–24 hours, preferably for 18 hours. The reduced compound is purified and crystallized by the methods known in the art to give 1-t-butoxycarbonyl±cis-2-[phenethyl]-5-[(3,4-methylenedioxy)benzoyl]pyrrolidine (VII).

Step 6. Step 6 describes the removal of the N-protecting group $R_2$ from the compound (VII).

A solution of 1-t-butoxycarbonyl±cis-2-[phenethyl]-5-[(3,4-methylenedioxy)benzoyl]pyrrolidine or otherwise 1-$R_2$-protected pyrrolidine (VII) in chlorinated hydrocarbon, preferably dry dichloromethane, is added to a strong protic acid, preferably trifluoroacetic acid. The reaction is carried on for 1–3 hours at room temperature. After purification and crystallization by methods known in the art, ±cis-2-[phenethyl]-5-[(3,4-methylenedioxy)benzoyl]pyrrolidine trifluoroacetate (VIII) is obtained.

Step 7. Step 7 describes the reduction of ±cis 2-[phenethyl]-5-[(3,4-methylenedioxy)benzoyl]pyrrolidine trifluoroacetate (VIII) to ±cis erythro 2-[phenethyl]-5-[(3,4-methylenedioxy)-α-hydroxybenzyl]pyrrolidine (IX).

Compound (VIII) is reduced to compound (IX) with a metal borohydride, preferably sodium borohydride dissolved in lower alcohol, preferably in ethanol at 0° temperature. The mixture is reacted for 0.5–3 hours and the solvent is removed. The aqueous residue is diluted with base such as sodium carbonate and the product is extracted with an organic solvent, preferably with ethyl acetate. The extract is washed with water, dried over sodium sulfate, purified, and crystallized by the methods known in the art to give ±cis erythro 2-[phenethyl]-5-[(3,4-methylenedioxy)-α-hydroxybenzyl]pyrrolidine (IX).

Reaction Scheme 2 illustrates preparation of cis threo 2-[phenethyl]-5-[(3,4-methylenedioxy)-α-hydroxybenzyl]pyrrolidine.

REACTION SCHEME 2

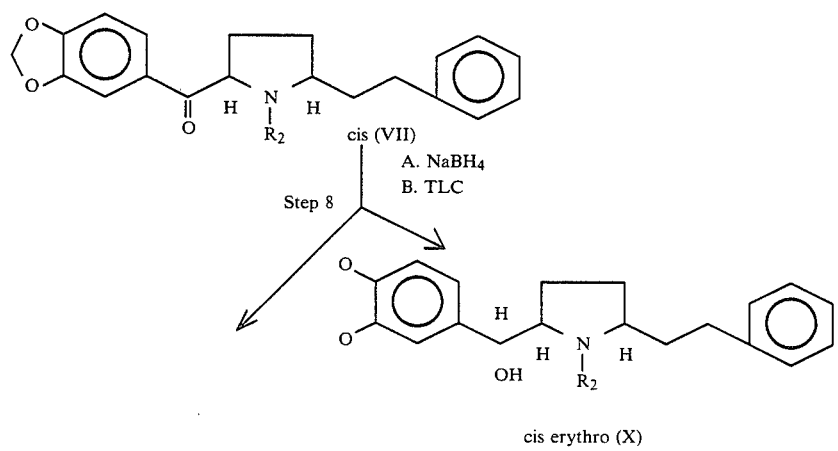

cis erythro (X)

REACTION SCHEME 2 -continued

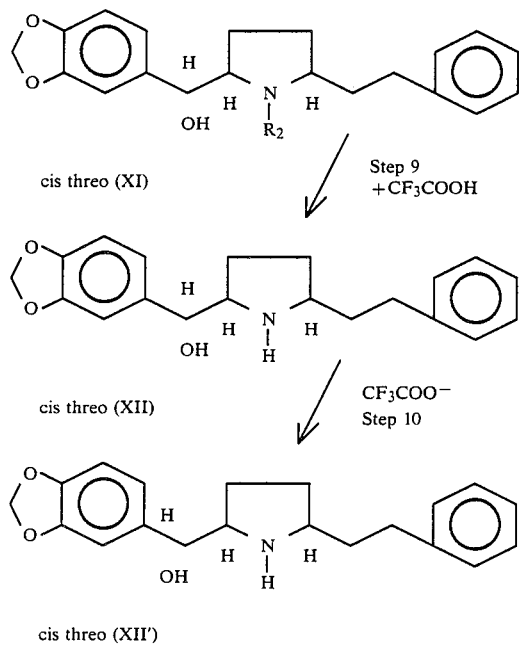

cis threo (XI)

Step 9
+CF₃COOH cis threo (XII)

CF₃COO⁻
Step 10 cis threo (XII')

Step 8. Step 8 describes the reduction of keto compound (VII) to the mixture of hydroxy compounds (X) and (XI) and subsequent separation of the obtained mixture into ±cis erythro isomer and ±cis threo isomer of 1-R₂-protected-2-[phenethyl]-5-[(3,4-methylenedioxy)-α-hydroxybenzyl]pyrrolidine (X) (XI), respectively.

Step 8A. 1-R₂-protected±cis 2-[phenethyl]-5-[(3,4-methylenedioxy)benzoyl]pyrrolidine (VII) (see Reaction Scheme 1) is reduced with metal borohydride, preferably with sodium borohydride, in lower alcohol, preferably ethanol or methanol, at −10° to +20° C., for 0.5–50 hours. The product obtained after purification by methods known in the art is the mixture of ±cis erythro and ±cis threo 2-[phenethyl]-5-[(3,4-methylenedioxy)-α-hydroxybenzyl]pyrolidines (X) and (XI), respectively.

Step 8B. Obtained mixture of cis erythro and cis threo isomers (X) and (XI) is separated by thin layer chromatography (TLC), column chromatography, crystallization or any other common separation technique, preferably by TLC, to obtain ±cis erythro 1-t-butoxycarbonyl-2-[phenethyl]-5-[(3,4-methylenedioxy)-α-hydroxybenzyl]pyrrolidine (X) and ±cis threo 1-t-butoxycarbonyl-2-[phenethyl]-5-[(3,4-methylenedioxy)-α-hydroxybenzyl]pyrrolidine (XI).

Cis erythro compound (X) is then submitted to Step 6 (Reaction Scheme 1) to remove N-protecting group R₂, to result in ±cis erythro 2-[phenethyl]-5-[(3,4-methylenedioxy)-α-hydroxybenzyl]pyrrolidine.

Step 9. Step 9 describes the removal of the N-protecting group from the ±cis threo 1-t-butoxycarbonyl-2-[phenethyl]-5-[(3,4-methylenedioxy)-α-hydroxybenzyl]pyrrolidine.

A solution of cis threo compound (XI) in chlorinated hydrocarbons, preferably dichloromethane, is added to a strong protic acid, such as hydrochloric acid or hydrobromic acid, preferably trifluoroacetic acid. The mixture is reacted for 1–50 hours at −10° to +20° C. temperature. The solvent is evaporated and the residue is purified to obtain ±cis threo 2-[(phenethyl]-5-[(3,4-methylenedioxy)-α-hydroxybenzyl]pyrrolidine trifluoroacetate(XII).

Step 10. Step 10 describes conversion of ±cis threo 2-[(phenethyl]-5-[(3,5-methylenedioxy)-α-hydroxybenzyl]pyrrolidine trifluoroacetate to a free base pyrrolidine (XII').

A trifluoroacetate salt (XII) is dissolved in a water and buffered, preferably with sodium bicarbonate. The resulting free base is extracted into an organic solvent, preferably ethyl acetate and purified by methods known in the art to yield ±cis threo 2-[(phenethyl]-5-[(3,4-methylenedioxy)-α-hydroxybenzyl]pyrrolidine.

REACTION SCHEME 3

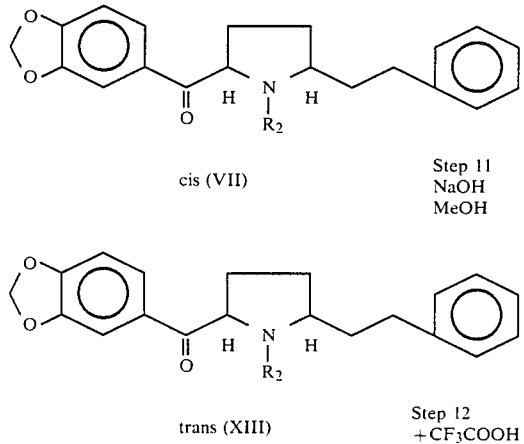

cis (VII)

Step 11
NaOH
MeOH trans (XIII)

Step 12
+CF₃COOH

-continued
REACTION SCHEME 3

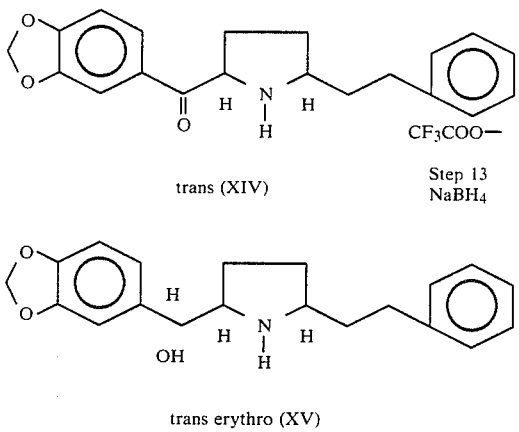

trans (XIV)

Step 13
NaBH₄ trans erythro (XV)

Reaction Scheme 3 illustrates the preparation of ±trans erythro 2-[phenethyl]-5-[(3,4-methylenedioxy)-α-hydroxybenzyl]pyrrolidines (XVI) and (XVII).

Step 11. Step 11 illustrates the isomerization of N-protected ±cis 2-[phenethyl]-5-[(3,4-methylenedioxy)benzoyl]pyrrolidine compound (VII) to the N-protected ±trans 2-[phenethyl]-5-[(3,4-methylenedioxy)benzoyl]pyrrolidine compound (XIII).

Isomerization is conducted under strong basic conditions, preferably with alkali hydroxides, such as sodium hydroxide or lithium hydroxide, in a suitable solvent system such as lower alkanol, for example methanol, ethanol, propanol, butanol and such, at the temperature of 20°–100° C., for the period of time 20–100 hours. The resulting mixture is rich in the trans isomer N-protected 2-[phenethyl]-5-[(3,4-methylenedioxy)benzoyl]pyrrolidine (XIII).

Step 12. Step 12 describes the removal of the N-protecting group from ±trans 2-[phenethyl]-5-[(3,4-methylenedioxy)benzoyl]pyrrolidine.

A solution of trans compound (XIII) in chlorinated hydrocarbons, preferably dichloromethane, is added to a strong protic acid, such as hydrochloric acid or hydrobromic acid, preferably trifluoroacetic acid. The mixture is reacted for 1–50 hours at −10° to +20° C. temperature. The solvent is evaporated and the residue is purified to obtain ±trans 2-[phenethyl]-5-[(3,4-methylenedioxy)benzoyl]pyrrolidine trifluoroacetate (XIV).

Step 13. Step 13 describes the reduction of trans 2-[phenethyl]-5-[(3,4-methylenedioxy)benzoyl]pyrrolidine compound (XIV) to ±trans erythro 2-[phenethyl]-5-[(3,4-methylenedioxy)-α-hydroxybenzyl]pyrrolidine (XV).

2-[phenethyl]-5-[(3,4-methylenedioxy)benzoyl]pyrrolidine trifluoroacetate (XIV) is reduced with metal borohydride, preferably with sodium borohydride, in a lower alcohol, preferably ethanol or methanol, at −10° to +20° C. The solvent is removed, the aqueous residue is diluted with the solution of base, preferably saturated sodium carbonate, and the product is extracted to organic halogenated solvent, preferably dichloromethane, to result in ±trans erythro 2-[phenethyl]-5-[(3,4-methylenedioxy)-α-hydroxybenzyl]pyrrolidine compound (XV).

REACTION SCHEME 4

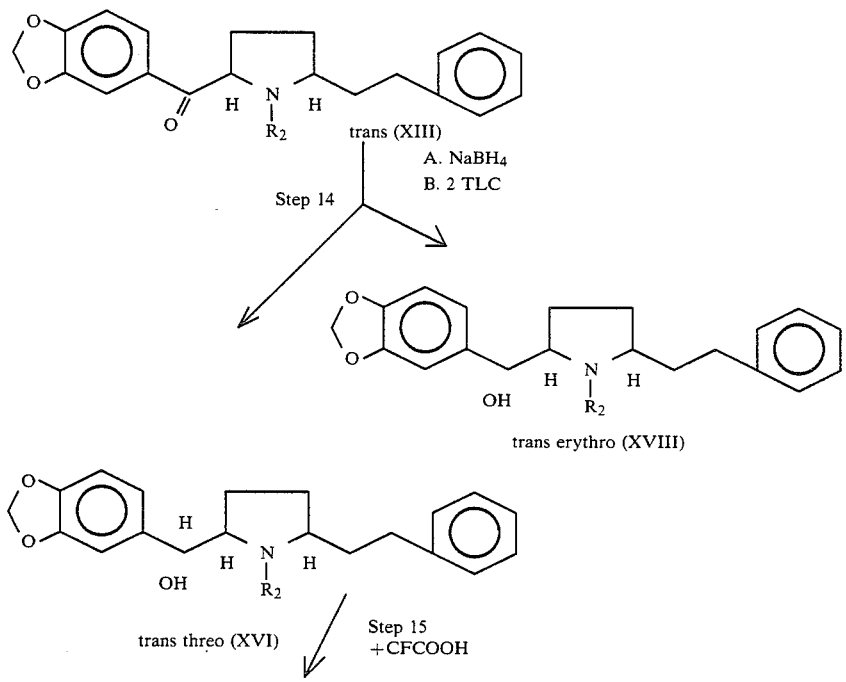

REACTION SCHEME 4 -continued

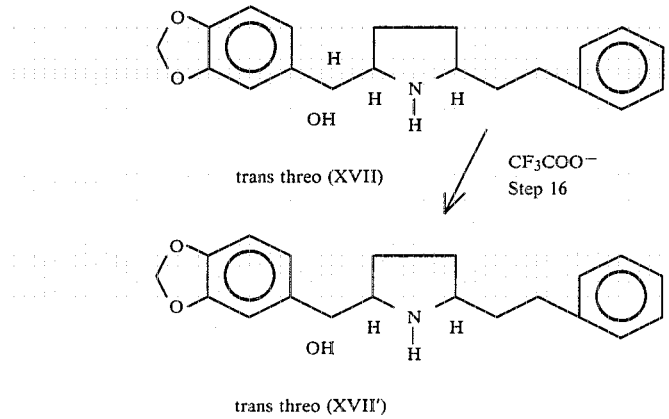

trans threo (XVII)

CF₃COO⁻
Step 16 trans threo (XVII')

Step 14. Step 14 describes the reduction of N-protected ±trans 2-[phenethyl]-5-[(3,4-methylenedioxy)benzoyl]pyrrolidine compound (XIII) into the N-protected ±trans erythro 2-[phenethyl]-5-[(3,4-methylenedioxy)-α-hydroxybenzyl]pyrrolidine (XV) and ±trans threo 2-[phenethyl]-5-[(3,4-methylenedioxy)-α-hydroxybenzyl]pyrrolidine (XVI).

Step 14A. The reaction begins with the reduction of compound (XIII) with metal borohydride, preferably with sodium borohydride, in lower alcohol, preferably ethanol or methanol, at −10° to +20° C. for 0.5-20 hours. The mixture obtained after purification by methods known in the art consist of ±trans erythro and ±trans threo N-protected 2-[phenethyl]-5-[(3,4-methylenedioxy)-α-hydroxybenzyl]pyrrolidine compounds (XVIII) and (XVI).

Step 14B. The obtained mixture is separated by TLC, column chromatography, crystallization or any other common separation technique, preferably by TLC, to obtain N-protected ±trans erythro 2-[phenethyl]-5-[(3,4-methylenedioxy)hydroxybenzyl]pyrrolidine (XVIII) and ±N-protected trans threo 2-[phenethyl]-5-[(3,4-methylenedioxy)-α-hydroxybenzyl]pyrrolidine (XVI).

N-protected ±trans erythro 2-[phenethyl]-5-[(3,4-methylenedioxy)-α-hydroxybenzyl]pyrrolidine (XVIII) is submitted to the procedure of Step 12 (Reaction Scheme 3).

Step 15. Step 15 describes the removal of the N-protecting group from the ±trans threo 2-[phenethyl]-5-[(3,4-methylenedioxy)-α-hydroxybenzyl]pyrrolidine compound (XVI).

A solution of N-protected trans 2-[phenethyl]-5-[(3,4-methylenedioxy)-α-hydroxybenzyl]pyrrolidine compound (XVI) in chlorinated hydrocarbons, preferably dichloromethane, is added to a strong protic acid, such as hydrochloric acid or hydrobromic acid, preferably trifluoroacetic acid. The mixture is reacted for 1-50 hours at −10° to +20° C. temperature. The solvent is evaporated and the residue is purified to obtain the trifluoroacetic acid salt of ±trans threo 2-[phenethyl]-5-[(3,4-methylenedioxy)-α-hydroxybenzyl]pyrrolidine (XX).

Step 16. Step 16 describes conversion of ±trans threo 2-[(phenethyl]-5-[(3,4-methylenedioxy)-α-hydroxybenzyl]pyrrolidine trifluoroacetate to a free base pyrrolidine (XII').

A trifluoroacetate salt (XII) is dissolved in a water and buffered, preferably with sodium bicarbonate. The resulting free base is extracted into an organic solvent, preferably ethyl acetate and purified by methods known in the art to yield ±trans threo 2-[(phenethyl]-5-[(3,4-methylenedioxy)-α-hydroxybenzyl]pyrrolidine.

Isolation, separation, and purification of the desired final compounds and their intermediates from the reaction mixture can be effected by any suitable separation or purification procedure, such as, for example, extraction, filtration, evaporation, distillation, crystallization, thin-layer chromatography, column chromatography, high pressure liquid chromatography, and the like, or by a combination of these procedures. If not otherwise described above, illustrations of suitable isolation, separation and purification procedures can be had by reference to the Examples herein below. However, other isolation, separation and isolation procedures could, of course, also be used.

In summary, compounds of this invention are prepared by the following steps:

N-protecting ±2-[phenethyl]-5-[(3,4-methylenedioxy)-benzyl]pyrrole;

reducing ±N-protected 2-[phenethyl]-5-[(3,4-methylenedioxy)benzoyl]pyrrole with noble metal catalyst under the mild reaction conditions to ±N-protected cis 2-[phenethyl]-5-[(3,4-methylenedioxy)-benzoyl]pyrrolidine;

removing N-protecting group from ±cis 2-[phenethyl]-5-[(3,4-methylenedioxy)benzoyl]pyrrolidine reducing cis ±2-[phenethyl]-5-[(3,4-methylenedioxy)-benzoyl]pyrrolidine to ±cis erythro 2-[phenethyl]-5-[(3,4-methylenedioxy)-α-hydroxybenzyl]pyrrolidine;

optionally converting ±cis N-protected 2-[phenethyl]-5-[(3,4-methylenedioxy)benzoyl]pyrrolidine to N-protected ±cis threo 2-[phenethyl]-5-[3,4-methylenedioxy)-α-hydroxybenzyl]pyrrolidine and subsequently removing N-protecting group;

optionally isomerazing ±N-protected cis 2-[phenethyl]-5-[(3,4-methylenedioxy)benzoyl]pyrrolidine to N-protected trans 2-[phenethyl]-5-[(3,4-methylenedioxy)benzoyl]pyrrolidine; and subsequently removing N-protecting group and reducing to ±trans erythro 2-[phenethyl]-5-[(3,4-methylenedioxy)-α-hydroxybenzyl]pyrrolidine;

optionally converting ±trans ±N-protected 2-[phenethyl]-5-[(3,4-methylenedioxy)benzoyl]pyrrolidine to N-protected ±trans threo 2-[phenethyl]-5-[(3,4-methylenedioxy)-α-hydroxybenzyl]pyrrolidine and subsequently removing N-protecting group;

optionally converting all isomers ±2-[phenethyl]-5-[(3,4-methylenedioxy)-α-hydroxybenzyl]pyrrolidine to a salt; and optionally converting salt to a base.

UTILITY AND ADMINISTRATION

Utility

The compounds of the invention are active antihypertensives. When administered orally or subcutaneously, in very small doses, they relieve hypertension in spontaneously hypertensive rats (SHR) but, at the same time, they do not affect rate and force of the heart beat. Accordingly, they are potentially useful as drugs for management of hypertension. They are also active as bronchodilators.

ADMINISTRATION

Administration of the active compounds and salts described herein can be via any of the accepted modes of administration for cardiovascular system regulating agents. These methods include oral or parenteral routes, such as intravenous, subcutaneous, intradermal, or intramuscular, but preferably oral mode of administration.

Parenteral route of administration is the administration of drugs to a patient by injection under or through one or more layers of the skin or mucous membrane. Parenteral administration would preferably be reserved for crisis situations, wherein the subject is unable to shallow or administer the medication to himself.

The amount of active ingredient administered will, of course, be dependent on the subject being treated, on the severity of the affliction, on the manner of administration and on the judgment of the prescribing physician. However, an effective dosage is in the range of 0.001–50 mg/kg/day, preferably 0.01–1 mg/kg/day. For an average 70 kg human, this would amount to 0.07–3500 mg per day, preferably 0.7–70 mg/day.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 0.1%–95% of active ingredient, preferably 1%–70%.

For parenteral administration, such as, for example, intravenous injections, the compound is dissolved in a vehicle. Vehicle may be, for example, aqueous vehicle, such as sodium chloride injection, Ringer's injection, dextrose injection and others, water miscible vehicle, such as ethyl alcohol, polyethylene glycol of the liquid series or propylne glycol, or nonaqueous vehicles such a corn oil, peanut oil or sesame oil. Vehicle will be buffered to the proper pH in order to stabilize a solution against chemical degradation and formed in such a way as to control isotonicity of injection. Other substances may also be added as antimicrobial or antioxidant agents.

For use as bronchodilators, administration of the active compounds and salts described herein can be via any of the accepted modes for bronchodilation, i.e., any mode described above can be used and compounds may also be administered in aerosol form.

PHARMACEUTICAL COMPOSITION

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient, and a compound of this invention or the pharmaceutically acceptable salt as an active ingredient thereof. In addition, it may include other medicinal or pharmaceutical agents, carriers, adjuvants, etc.

The composition or formulation to be administered will, in any event, contain a quantity of the active ingredient(s) in an amount effective to alleviate the symptoms of the subject being treated.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like. The active ingredient as defined above may also be formulated as suppositories, using as the carrier for example polyalkylene glycols, such as propylene glycol.

Liquid pharmaceutically administerable compositions can be prepared by dissolving or dispersing, or otherwise preparing an active ingredient (as defined above), and mixing it optionally with a pharmaceutical adjuvant in a carrier, such as, for example, water, saline, aqueous dextrose, glycerol, ethanol, and the like, to thereby form a solution or suspension.

If desired, the pharmaceutical composition to be administered may also contain minor amounts of nontoxic auxiliary substances such as wetting or emulsifying agents, pH buffering agents and the like, such as for example, sodium acetate, sorbitan monolaurate, triethanolamine sodium acetate, sorbitan monolaurate, triethanolamine oleate, etc.

Methods of preparing various pharmaceutical compositions with certain amount of active ingredients are known, or will be apparent, to those skilled in this art. For examples, see *Remington's Pharmaceutical Sciences*, Mack Publishing Company, Easton, Pa., 15th Edition (1975).

The Roman numerals in Examples correspond to a Roman numerals in Reaction Schemes and in Preparation Procedures.

EXAMPLE 1

Preparation of 3,4-Methylenedioxybenzoylmorpholide (I)

To a suspension of 11.15 g of 3,4-methylenedioxybenzoic acid (Trans World Chem.) in 250 ml of dichloromethane was added 2.87 ml of thionyl chloride and 1 ml of dimethylformamide. The mixture was stirred at room temperature for approximately 15 min. or until solution occurred. The solvent was removed in vacuo. The residual acid chloride was dissolved in ether, and 5.8 ml of morpholine was added slowly with stirring. The precipitate was removed by filtration. The ether was evaporated in vacuo to give 11.4 g of an oil which was purified by column chromatography in silica gel with ethyl acetate-hexane (2:3) as the eluting solvent. 3,4- methylenedioxybenzoylmorpholide (I) was obtained. (Step 3)

EXAMPLE 2

Preparation of Phenylacetylmorpholide (IIa)

4 ml of thionyl chloride and 0.5 ml of dry dimethylformamide were added to a solution of 12.5 g of phenylacetic acid (Sigma) in 200 ml of dry dichloromethane. The solution was stirred for 15 minutes and evaporated to dryness in vacuo. The residual acid chloride was dissolved in 100 ml of dry dichloromethane. A solution of 5.35 ml of morpholine in 100 ml of dichloromethane was added dropwise with stirring. When the addition was ended, the mixture was evaporated to dryness in vacuo and the residue was percolated through a short silica gel column using ethyl acetate-hexane (3:7) as the percolating solvent. 13.7 g of phenylacetylmorpholide (IIa) was obtained, m.p. 64°–66° C. (Step 1)

EXAMPLE 3

Preparation of 2-Phenylacetylpyrrole (III)

Vilsmeier-Haack reaction was carried out according to the method of J. White and G. McGillivray, *J. Org. Chem.*, 42, 4248 (1979).

A mixture of 30 g (0.146 mole) of phenylacetylmorpholide and 27 ml (0.295 mole) of phorphorous oxychloride was stirred magnetically at room temperature in a nitrogen atmosphere for 6 h. A solution of 10 ml (0.149 mole) of pyrrole in 700 ml of anhydrous 1,2-dichloroethane was added at a rate such that the temperature did not exceed 30°. The reaction mixture was stirred at room temperature for 18 h. The mixture was cautiously mixed with a solution of 700 ml of 10% sodium carbonate in water and the mixture was heated at reflux temperature with stirring for 1.5 h. The cooled mixture was filtered through celite. The organic phase was separated and combined with dichloromethane extracts (3×500 ml) of the aqueous phase, the organic phases were dried over sodium sulfate and evaporated in vacuo. The residue was subjected to column chromatography over silica gel (1 kg) 9.6 g (35%) of 2-phenylacetylpyrrole (III) was eluted with dichloromethane and crystallized from acetone-hexane, m.p. 92°–94°. (Step 1)

EXAMPLE 4

Preparation of 2-[Phenethyl]Pyrrole (IV)

A solution of 6.00 g (0.032 mole) of the 2-phenylacetylpyrrole (III) in 200 ml of anhydrous tetrahydrofuran was added to a suspension of 600 g (0.153 mole) of lithium aluminum hydride in dry tetrahydrofuran. The mixture was stirred at reflux temperature for 48 h. The mixture was cooled to 0°, ethyl acetate was cautiously added to destroy the excess hydride and then saturated aqueous sodium sulfate was added. The organic phase was decanted, dried over sodium sulfate and evaporated in vacuo. The residue was subjected to column chromatography on neutral alumina (Fluka, Act II). 4.800 g (88%) of 2-[phenethyl]pyrrole (IV) was eluted with hexane-ethyl acetate and crystallized, m.p. 40°–42° (hexane). (Step 2).

EXAMPLE 5

Preparation of ±2-[Phenethyl]-5-[(3,4-Methylenedioxy)Benzoyl]Pyrrole (V)

A mixture of 12,3 g (0.046 mole) of [(3,4-methylenedioxy)benzoyl]morpholide (I) and 12 ml (0.13 mole) of phosphorous oxychloride was stirred at room temperature for 3 h in a nitrogen atmosphere. A solution of 10.0 g (0.058 mole) of 2-[phenethyl]pyrrole (IV) in 200 ml of dry 1,2-dichloroethane was added and the mixture was stirred at room temperature for 18 h. The reaction mixture was stirred at room temperature for 18 h. The mixture was cautiously mixed with a solution of 700 ml of 10% sodium carbonate in water and the mixture was heated at reflux temperature with stirring for 1.5 h. The cooled mixture was filtered through celite. The organic phase was separated and combined with dichloromethane extracts (3×500 ml) of the aqueous phase, the organic phases were dried over sodium sulfate and evaporated in vacuo. The residue was submitted to column chromatography on neutral alumina (Fluka, Act II). The crude product was purified by column chromatography on silica gel (1 kg). The desired material was eluted with dichloromethane to give a 5.58 g (38%) of ±2-[phenethyl]-5-[(3,4-methylenedioxy)benzoyl]pyrrole (V) which was crystallized from dichloromethane-acetone, m.p. 143°–145° (dichloromethaneacetone). (Step 3)

EXAMPLE 6

Preparation of 1-t-Butoxycarbonyl±2-[Phenethyl]-5-[(3,4-Methylenedioxy)Benzoyl]Pyrrole (VI)

4.10 g (0.012 mole) of ±2-[phenethyl]-5-[(3,4-methylenedioxy)benzoyl]pyrrole (V) was added to a 1.40 g of suspension (0.05 mole; 60% dispersion in mineral oil) of sodium hydride in 100 ml of dry dimethylformamide. The mixture was heated at 45°–60° for 2 h. 4.51 g (0.02 mole) of di-t-butyl dicarbonate was added rapidly and the solution was stirred at 60°–70° for 2 h. The reaction mixture was cooled, poured onto ice-water and the product was extracted into ethyl acetate. The extract was washed with water, dried over sodium sulfate and evaporated in vacuo. Then it was purified by column chromatography in alumina (300 g, Fluka, Neutral Act. II). The crude product was crystallized from acetone-hexane to give the 5.0 g (94%) of ±1-t-butoxycarbonyl-2[phenethyl]-5-[(3,4-methylenedioxy)benzoyl]pyrrole (VI), m.p. 145°–147° (acetone-hexane). (Step 4)

EXAMPLE 7

Preparation of 1-t-Butoxycarbonyl ±Cis 2-[Phenethyl]-5-[(3,4-Methylenedioxy)Benzoyl]Pyrrolidine (VII)

A solution of 4.50 g, (0.01 mole) 1-t-butoxycarbonyl-±2-[phenethyl]-5-[(3,4-methylenedioxy)benzoyl]pyrrole (VI) in 300 ml of ethanol-ethyl acetate (2:1) containing 1.8 g of suspended platinic oxide was hydrogenated at room temperature and atmospheric pressure for 18 h. The reaction mixture was filtered, the filtrate was evaporated in vacuo and the residue was subjected to column chromatography on neutral alumina (Fluka, Act II). The product was eluted with hexane-ethyl acetate (95:5). The crude 1-t-butoxycarbonyl ±cis 2-

[phenethyl]-5-[(3,4-methylenedioxy)benzoyl]pyrrolidine (VII) was obtained in quantitative yield as an oil. Oil. (Step 5)

Oil

U.V. (MeOH), 215, 221 sh, 233, 276, 288 sh, 311, 299 sh nm (ε 8910; 9330; 13,200; 6030); 4270; 6760; 5370).

I.R. (CHCl$_3$) 1756, EM-390, 1.37 (s, 9H, t-butyl, 1.48–1.86 (m, 5H), 2.28 (m, 1H), 2.71 (m, 2H), 4.00 (m, 1H, 5.20 (m, 1H), 6.01 (s, 2H,)CH$_2$O), 6.83 (d, 1H, J=7.5 Hz, aromatic hydrogen), 7.25 (s, 5H, aromatic hydrogens), 7.75 (m, 2H, aromatic hydrogens.

EXAMPLE 8

Preparation of ±Cis 2-[Phenethyl]-5-[(3,4-Methylenedioxy)Benzoyl]Pyrrolidine Trifluoroacetate (VIII)

50 ml of trifluoroacetic acid was added to a solution of 3.60 g (0.0085 mole) of 1-t-butoxycarbonylcis 2-[phenethyl]-5-[(3,4-methylenedioxy)benzoyl]pyrrolidine (VII) in 200 ml of dry dichloromethane. The reaction solution was stirred at room temperature for 0.5 h. The solvent was removed in vacuo and the residue was crystallized from dichloromethane-ether to give 2.90 g (73%) of ±cis 2-[phenethyl]-5-[(3,4-methylenedioxy)benzoyl]pyrrolidine trifluoroacetate (VIII), m.p. 166°–168° (dichloromethane-ether). (Step 6)

EXAMPLE 9

Preparation of ±Cis Erythro 2-[2-Phenethyl]-5-[(3,4-Methylenedioxy)-α-hydroxybenzyl]Pyrrolidine (IX)

1.35 g (0.035 mole) of sodium borohydride was added to a stirred solution of 2.70 g (0.0057 mole) of ±cis 2-[phenethyl]-5-[(3,4-methylenedioxy)benzoyl]pyrrolidine in 270 ml ethanol, at 0° temperature. After 1 hour at 0°, the mixture was poured into 100 ml of 10% ammonium chloride solution. The mixture was evaporated in vacuo to remove the ethanol, the residue was cooled to 0°, and 50 ml of a saturated sodium carbonate solution was added. The product was extracted into ethyl acetate, the extract was washed with water, dried over sodium sulfate and evaporated in vacuo. The residue was crystallized from ethyl acetate-hexane to give 1.72 g (93%) of the desired ±cis erythro 2-[phenethyl]-5-[(3,4-methylenedioxy)-α-hydroxybenzyl]pyrrolidine (IX), m.p. 122°–123° (dichloromethane-hexane). (Step 7)

EXAMPLE 10

Preparation of ±Cis Erythro and ±Cis Threo 1-t-Butoxycarbonyl-2-[Phenethyl]-5-[(3,4-Methylenedioxy)α-Hydroxybenzyl]Pyrrolidine (X) and (XI)

A solution of 3.20 g (4.5 mmole) of the cis 1-t-butoxycarbonyl-2[phenethyl]-5-[(3,4-methylenedioxy)benzoyl]pyrrolidine (VII), prepared in Example 7 and 6.4 g (16.9 mmole) of sodium borohydride in 300 ml of ethanol is heated at a reflux temperature for 45 min. The solvent is removed in vacuo and the residue is partitioned between water and ethyl acetate. The organic phase is evaporated in vacuo and the residue is percolated through a short column of silica gel using ethyl acetate-hexane (1:3) as the percolating solvent.

The resulting mixture is separated by TLC with ethyl acetate/hexane (1:3) into two isomers:

±cis erythro 1-t-butoxycarbonyl-2-[phenethyl]-5-[(3,4-methylenedioxy)-α-hydroxybenzyl]pyrrolidine and ±cis threo 1-t-butoxycarbonyl-2-[phenethyl]-5-[(3,4-methylenedioxy)-α-hydroxybenzyl]pyrrolidine. (Step 8)

The same procedure is used for the preparation of trans erythro (XVIII) and trans threo (XVI) compounds (shown in Reaction Scheme 4) (Step 14)

The resulting compounds are:

±trans erythro 1-t-butoxycarbonyl-2-[phenethyl]-5-[(3,4-methylenedioxy)-α-hydroxybenzyl]pyrrolidine and ±trans threo 1-t-butoxycarbonyl-2-[phenethyl]-5-[(3,4-methylenedioxy)-α-hydroxybenzyl]pyrrolidine.

EXAMPLE 11

Removal of N-Protecting Group from ±Cis Erythro or ±Cis Threo 1-t-Butoxycarbonyl-2-[Phenethyl]-5-[(3,4-Methylenedioxy)-α-Hydroxybenzyl]Pyrrolidine (X) (XI)

50 ml of trifluoroacetic acid is added to a solution of ±cis erythro 1-t-butoxycarbonyl-2-[phenethyl]-5-[(3,4-methylenedioxy)-α-hydroxybenzyl]pyrrolidine (X) or to a solution of 3.60 g (0.0085 mole) ±cis threo 1-t-butoxycarbonyl-[phenethyl]-5-[(3,4-methylenedioxy)-α-hydroxybenzyl]pyrrolidine (XI) in 200 ml of dichloromethane. The reaction mixture is stirred at room temperature for 0.5–1 hour. The solvent is removed in vacuo and the residue is crystallized from dichloromethane-ether to give trifluoroacetic acid salt of compounds (X) and (XI), resulting in:

±cis erythro 2-[phenethyl]-5-[(3,4-methylenedioxy)-α-hydroxybenzyl]pyrrolidine trifluoroacetate (IX); and ±cis threo 2-[phenethyl]-5-[(3,4-methylenedioxy)-α-hydroxybenzyl]pyrrolidine trifluoroacetate (XII). (Step 9)

The same procedure is used for the removal of N-protecting group from compounds (XIII), (XVI), and (XVIII), shown in Reaction Schemes 3 and 4.

EXAMPLE 12

Preparation of Trans 1-t-Butoxycarbonyl-2-[Phenethyl]-5-[(3,4-Methylenedioxy)Benzoyl]Pyrrolidine (XIII)

A solution of 50 g of cis pyrrolidine (VII) prepared in Example 7 in a solvent mixture consisting of 2.25 ml of 2-propanol and 100 ml of 10% aqueous sodium hydroxide is heated at reflux temperature for 26 hours. The solution is evaporated to dryness, water is added to the residue and the mixture is extracted with ethyl acetate. The solvent is evaporated and the residue is separated by column chromatography (silica gel/1 Kg/one meter column). The column is developed with ethyl acetate/hexane (1:4) to give, as the first fraction, the ±trans 1-t-butoxycarbonyl-2-[phenethyl]-5-[(3,4-methylenedioxy)benzoyl]pyrrolidine (XIII) and as a second fraction nonconverted cis isomer (VII).

EXAMPLE 13

Conversion of Free Base to Salt Preparation of 2-[Phenethyl]-5-[(3,4-Methylendioxy)α-Hydroxybenzyl]Pyrrolidine Hydrochloride Excess 3% hydrogen chloride in methanol is added to a solution of 1.0 g of ±2-[phenethyl]-5-[(3,4-methylenedioxy)-α-hydroxybenzyl]pyrrolidine in 20 ml of methanol. Diethyl ether is added until precipitation is complete. ±2-phenethyl]-5-[(3,4-methylenedioxy)-α- hydroxybenzyl]pyrrolidine hydrochloride is filtered, washed with ether, air dried and recrystallized.

EXAMPLE 14

Conversion of Salt to Free Base Preparation of ±2-[Phenethyl]-5-[(3,4-Methylenedioxy)-α-Hydroxybenzyl]Pyrrolidine 1.0 g of ±2-[phenethyl]-5-[(3,4-methylenedioxy)-α-hydroxybenzyl]pyrrolidine hydrochloride or trifluoroacetate (XII') and (XVII'), is dissolved in 50 ml of water. A solution of sodium bicarbonate is added, and the pH adjusted to about pH 5. The resulting free base is extracted with ethyl acetate, the organic layer is then separated, washed twice with water, dried over magnesium sulfate and evaporated to yield ±2-[phenethyl]-5-[(3,4-methylenedioxy)-α-hydroxybenzyl)]pyrrolidine as the free base.

EXAMPLE 15

Direct interchange of acid addition salts 1 g of ±2-[phenethyl]-5-[(3,4-methylenedioxy)-α-hydroxybenzyl]pyrrolidine acetate, prepared according to Example 15, is dissolved in a solution of 1 ml 50% aqueous sulfuric acid in 10 ml ethanol and the resulting precipitate is harvested. The product is suspended in ethanol and filtered, air dried, and recrystallized from methanol/acetone to yield ±2-[phenethyl]-5-[(3,4-methylenedioxy)-α-hydroxybenzyl]pyrrolidine bisulfate.

In Examples 16–23, the active ingredient is ±cis erythro 2-[phenethyl]-5-[(3,4-methylenedioxy)-α-hydroxybenzyl]pyrrolidine hydrochloride.

EXAMPLE 16

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 17

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 18

| Ingredients | Quantity per tablet, mgs. |
| --- | --- |
| Active ingredient | 200 |
| cornstarch | 50 |
| lactose | 145 |
| magnesium stearate | 5 |

The above ingredients are mixed intimately and pressed into single scored tablets.

EXAMPLE 19

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 20

| Ingredients | Quantity per tablet, mgs. |
| --- | --- |
| Active ingredient | 150 |
| lactose | 92 |

The above ingredients are mixed and introduced into a hard-shell gelatin capsule.

EXAMPLE 21

An injectable preparation buffered to a pH of 7 is prepared having the following composition:

| Ingredients | |
| --- | --- |
| Active ingredient | 0.2 g |
| $KH_2PO_4$ buffer (0.4 M solution) | 2 ml |
| KOH (1 N) | q.s. to pH 7 |
| water (distilled, sterile) | q.s. to 20 ml |
| 5351J | |

EXAMPLE 22

An oral suspension is prepared having the following composition:

| Ingredients | |
| --- | --- |
| Active Ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water q.s. to | 100 ml |

EXAMPLE 23

| | |
| --- | --- |
| Active ingredient | 3.0% |
| Span$^R$ 85 (sorbitan trioleate) | 1.0% |
| Freon 11 (trichloromonofluoromethane) | 30.0% |
| Freon 114 (dichlorotetrafluoroethane) | 41.0% |
| Freon 12 (dichlorodifluoromethane) | 25.0% |

EXAMPLE 24

Antihypertensive Activity of ±Cis Erythro 2-[Phenethyl]]-5-[(3,4-Methylenedioxy)-α-Hydroxybenzyl]Pyrrolidine This example illustrates superior antihypertensive activity of compounds of this invention. In this Example, I, II, III, or IV mean compounds as shown in Tables 1 and 2.

24 previously trained adult male spontaneously hypertensive rats were distributed into 6 groups (5 animals per group) with approximately equal mean systolic blood pressures. The 6 groups were then studied concurrently in a 2-day compound screening procedure.

Test compounds were randomly assigned to each group. 5 groups received potential antihypertensive agents and 1 control group received vehicle only (water and Tween).

At approximately 17 hours prior to the first day of dosing food was removed from the rat cages. On the morning of Day 1, a group of 4 rats was orally dosed (by gavage) with 12.5 mg/kg or 25 mg/kg of ±cis erythro 2-[phenethyl]-5-[(3,4-methylenedioxy)]-α-hydroxybenzyl)pyrrolidine (I), or other tested compound, dissolved/suspended in water (using 2-3 drops Tween 80) with a homogenizer at concentrations such that 0.1 ml of solution was administered per 10 g of body weight. At 4½ hours post dose, food was put back in the cages and the rats were allowed to eat for 2½ hours, after which food was again removed. On the morning of Day 2, rats were orally dosed as described above. Immediately after dosing, the rats were put in restrainers and placed in a heated chamber (30±1.0° C.) for four hours. Normal feeding resumed at the end of the study on Day 2.

Systolic blood pressure (i.e., pressure at the appearance of the first pulse) were recorded using photoelectric transducers. The coccygeal arteries of 3 rats (in a horizontal group) were simultaneously occluded by pump-inflated tail cuffs that were automatically inflated to 300 mmHg and then deflated. A pressure curve and tail pulses were simultaneously monitored on an MFE recorder. Four consecutive (at 30 second intervals) traces were recorded for each rat in a given horizontal group at one, two, three and four hours post compound administration. Subsequent horizontal groups were automatically tested in the same manner.

The mean systolic blood pressure (SBP) of each rat at each observation time was calculated. The SBP of the animals in each dose group were compared to the SBP of the animals in the control group (vehicle only) at each observation time using a one-way analysis of variance test. A compound exhibiting $p \leq 0.05$ at any observation time was considered to exhibit significant antihypertensive activity. Compounds significantly decreasing blood pressure 20 mmHg or more from control values at all four observation times were considered worthy of further examination. In these instances heart rates were calculated and tested for significant change from control heart rate values using the two-tailed test. Pressures were read at hours 1, 2, 3 and 4 after dosing on both days 1 and 2.

A. Table 1 summarizes the results obtained by testing three structurally similar compounds, namely, ±cis erythro 2-[phenethyl]-5-[(3,4-methylenedioxy)-α-hydroxybenzyl]pyrrolidine (I); ±cis erythro 2-[phenethyl]-5-[(3,4-dihydroxy)-α-hydroxybenzyl]pyrrolidine (II) and ±trans erythro-2-[phenethyl]-5-[(3,4-dihydroxyphenyl)-α-hydroxymethyl]pyrrolidine (III).

TABLE 1

| | | | | | | | | | | | | | | | | |
|---|---|---|---|---|---|---|---|---|---|---|---|---|---|---|---|---|
| | ±cis erythro 2-[phenethyl]-5-[(3,4-methylenedioxy)-α-hydroxybenzyl]pyrrolidine Compound I | | | | | | ±cis erythro 2-[phenethyl]-5-[(3,4-dihydroxy)-α-hydroxybenzyl]pyrrolidine Compound II | | | | | | ±trans erythro 2-[phenethyl]-5-[3,4-dihydroxy)-α-hydroxybenzyl]pyrrolidine Compound III | | | |
| | per os | | | 25 mg/kg | | | per os | | | 25 mg/kg | | | per os | | | 25 mg/kg | | |
| | Systolic Blood Pressure | | | Heart Rates | | Systolic Blood Pressure | | | Heart Rates | | | Systolic Blood Pressure | | | Heart Rates | |
| | % | p | mm Hg | % | p | BPM | % | p | mm Hg | % | p | BPM | % | p | mm Hg | % | p | BPM |
| Hours 1 | −35 | 0.001 | −80 | 2 | NS | 5 | −27 | 0.05 | −54 | 47 | 0.05 | 148 | −31 | 0.01 | −62 | 24 | 0.02 | 73 |
| Past 2 | −33 | 0.03 | −69 | −4 | NS | −12 | −40 | 0.05 | −87 | 41 | 0.05 | 125 | −27 | 0.01 | −54 | 32 | 0.01 | 84 |
| Dosing 3 | −35 | 0.03 | −72 | −6 | NS | −17 | −43 | 0.05 | −89 | 29 | 0.05 | 90 | −18 | 0.02 | −34 | 10 | NS | 26 |
| 4 | −35 | 0.01 | −74 | −18 | NS | −55 | −39 | 0.05 | −79 | 32 | 0.05 | 96 | −31 | 0.001 | −69 | −1 | NS | −3 |

BPM means beats per minute;
Δmm Hg means difference in blood pressure expressed in mm Hg;
% Δ means difference in blood pressure expressed in %;
p = significance.

Table 1 illustrates the superiority of compound I ±cis erythro 2-[phenethyl]-5-[(3,4-methylenedioxy)-α-hydroxybenzyl]pyrrolidine over compounds II ±cis erythro 2-[phenethyl]-5-[3,4-dihydroxy)-α-hydroxybenzyl]pyrrolidine and III ±trans erythro 2-[phenethyl]-5-[3,4-dihyroxy)-α-hydroxybenzyl)pyrolidine.

Compound I significantly decreases systolic blood pressure without, at the same time, increasing the heart rate. Increasing the heart rate is an undesirable condition very often associated with decreasing of blood pressure.

Compound II also significantly decreases systolic blood pressure. However, the decrease in systolic blood pressure caused by compound II is accompanied by very high increase in the heart rate. Increased heart beat persists during all four hours.

Compound III also significantly decreases blood pressure although not as much and not as steadily as compound I. However, the decrease in systolic blood pressure caused by compound III is accompanied by significant increase in the heart beat during the first two hours after dosing.

B. Table 2 summarizes the results obtained by testing two structurally similar compounds, namely, ±cis erythro 2-[phenethyl]-5-[(3,4-methylenedioxy)-α-hydroxybenzyl]pyrrolidine I and ±cis erythro 2-[(3,4-dimethoxy)phenethyl]-5-[(3,4-methylenedioxy)-α-hydroxybenzyl]pyrrolidine (IV).

TABLE 2

| | | ±cis erythro 2-[phenethyl]-5-[(3,4-methylenedioxy)-α-hydroxybenzyl]pyrrolidine Compound I | | | | | | ±cis erythro 2-[(3,4-dimethoxy)phenethyl]-5-[(3,4-methylenedioxy)-α-hydroxybenzyl]pyrrolidine Compound IV | | | | | |
|---|---|---|---|---|---|---|---|---|---|---|---|---|---|
| | | per os | | 12.5 mg/kg | | | | per os | | 12.5 mg/kg | | | |
| | | Systolic Blood Pressure | | | Heart Rates | | | Systolic Blood Pressure | | | Heart Rates | | |
| | | % | p | mm Hg | % | p | BPM | % | p | mm Hg | % | p | BPM |
| Hours | 1 | −25 | NS | −48 | 18 | NS | 52 | −9 | NS | 17 | 15 | NS | +45 |
| Past | 2 | −26 | 0.05 | −51 | 5 | NS | 13 | −19 | 0.05 | −42 | 12 | NS | +34 |
| Dosing | 3 | −29 | 0.05 | −61 | −9 | NS | −28 | −16 | NS | −33 | −4 | NS | +13 |
| | 4 | −70 | 0.05 | −91 | −13 | 0.05 | −39 | −25 | 0.05 | −57 | −12 | 0.05 | −34 |
| | 8 | −18 | 0.05 | −39 | +2 | NS | 7 | −17 | NS | −35 | −1 | NS | −2 |
| | 12 | −2 | NS | −4 | +5 | NS | 13 | −11 | NS | −18 | −8 | NS | −21 |

% Δ, p, Δmm Hg and BPM are as in Table 1.

Compound I ±cis erythro 2-[phenethyl]-5-[(3,4-methylenedioxy)-α-hydroxybenzyl]pyrrolidine and compound IV, ±cis erythro 2-[3,4-dimethoxy)phenethyl]-5-[(3,4-methylenedioxy)-α-hydroxybenzyl]pyrrolidine were tested using the same antihypertensive test as described above. Only half of the dose used in Table 1, i.e., 12,5 mg/kg dosage was used.

Compound I shows, even at the low dosage of 12,5 mg/kg, a very strong blood pressure lowering effect which lasts more than eight hours following the single dosage. From the second hour until the eighth hour the decrease in systolic blood pressure is significant. Although some increase in the heart rate was observed during the first two hours, this increase was not significant and it quickly normalized. During the third and fourth hour, the heartbeat actually decreased and from 4–12 hours the heartbeat was close to normal.

Compound IV, on the other hand had much less effect on lowering of the systolic blood pressure. Heart rates, while higher in absolute numbers than those of compound I, were also not significantly increased.

CONCLUSION

Among four closely structurally related compounds compound I has the surprising and unexpectedly high effect on lowering of systolic blood pressure which is not accompanied simultaneously with the increase in the heart rate. The two other compounds II and III also show effect on lowering of systolic blood pressure. Both of them, however, at the same time, increase heart rates. Such increase is undesirable. It forces the heart to pulsate faster forcing the higher volumes of the blood into the peripheral circulation. More rapidly pulsating heart is susceptible to exhaustion and cardiac failure. Also, increased blood volume pumped more rapidly to the periphery can cause increased blood pressure by way of the feedback.

Compound IV which is also structurally similar to compound I has only mild systolic blood pressure decreasing effect. At the same time, however, it slightly increases heart rates.

Thus among four closely related compounds, compound I is the only compound which lowers the systolic blood pressure significantly and, at the same time, does not increase the heart rate. These two features make compound I desirable antihypertensive.

EXAMPLE 25

Postural Hypotensive Effects of 2-[Phenethyl]-5-[(3,4-Methylenedioxy)-α-Hydroxybenzyl]Pyrrolidine This example illustrates postural hypotensive effect of compounds of this invention.

Male normotensive Sprague-Dawley rats (Charles River) weighing 250–300 g were used. Surgery was conducted when the rats were under ether anesthesia. The left femoral artery and vein were cannulated for the measurement of blood pressure and for drug administration, respectively. The rats were secured on their backs to a special tilt table and allowed to recover from anesthesia. Animals were tilted from the horizontal to the head-up vertical position (90°) for 2 minutes twice at 15 minute intervals during the control period and at 15, 30, 45, 60 min. after drug administration.

Compounds were prepared in water and were administered orally by gavage. Injection volume was 1 ml/100 g. Each rat received only a single dose of a compound.

The hypotensive response is the maximal mean blood pressure lowering induced by the drug with the animal in the supine position. The postural hypotensive effect is the maximal drop in MBP in response to tilting (i.e., the net drop in BP in reference to that prior to tilt). Responses are expressed as absolute changes in mmHg.

The results are shown in FIG. 1.

±Cis erythro 2-[[phenethyl]-5-[(3,4-methylenedioxy)-α-hydroxybenzyl]pyrrolidine induced a dose-dependent hypotensive response (1–100 mg/kg, p.o.). At 10 mg/kg (p.o.), the compound lowered blood pressure 45 mmHg and at 100 mg/kg (p.o.), magnitude of 20–30 mmHg within the dose range tested.

Thus, the compound I is, in a very small dose, very effective in lowering blood pressure in normotensive rats. This finding supports the results shown in Example 24 and the conclusion that Compound I is the desirable antihypertensive.

What is claimed is:

1. A compound of the formula

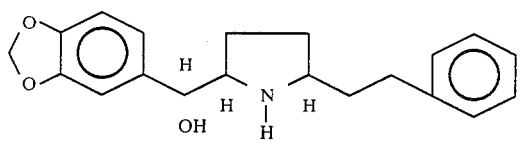

namely, ±2-[phenethyl]-5-[(3,4-methylenedioxy)-α-hydroxybenzyl]pyrrolidine and the pharmaceutically acceptable acid addition salts thereof.

2. The compound of claim 1 wherein the compound is a cis isomer.

3. A compound of the formula

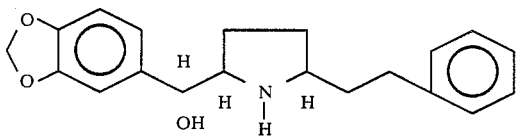

and its enantiomer, namely, (±), (+), and (−) cis erythro 2-[phenethyl]-5-[(3,4-methylenedioxy)-α-hydroxybenzyl]pyrrolidine and the pharmaceutically acceptable acid addition salts thereof.

4. A compound of the formula

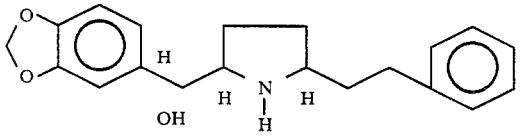

and its enantiomer, namely, (±), (+), and (−) cis threo 2-[phenethyl]-5-[(3,4-methylenedioxy)-α-hydroxybenzyl]pyrrolidine and the pharmaceutically acceptable acid addition salts thereof.

5. The compound of claim 1 wherein the compound is a trans isomer.

6. A compound of the formula

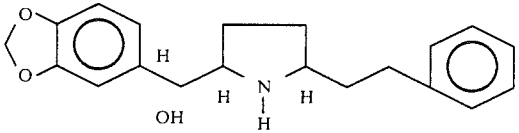

and its enantiomer, namely, (±), (+), and (−)trans erythro 2-[phenethyl]-5-[(3,4-methylenedioxy)-α-hydroxybenzyl]pyrrolidine and the pharmaceutically acceptable acid addition salts thereof.

7. A compound of the formula

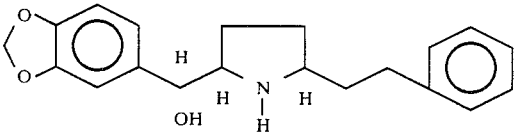

and its enantiomer, namely, (±), (+), and (−)trans threo 2-[phenethyl]-5-[(3,4-methylenedioxy)-α-hydroxybenzyl]pyrrolidine and the pharmaceutically acceptable acid addition salts thereof.

8. A pharmaceutical composition which comprises a therapeutically effective amount of a compound of formula

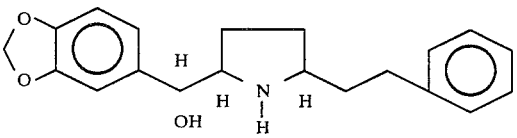

and the pharmaceutically acceptable acid addition salts in admixture with a pharmaceutically acceptable excipient.

9. A method for regulating hypertension in mammals which method comprises administering to a subject in need of such treatment a therapeutically effective amount of the compound of the formula

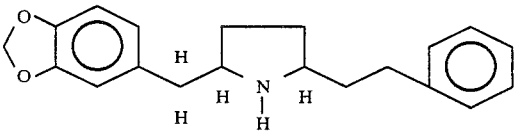

and the pharmaceutically acceptable acid addition salts thereof.

* * * * *